(12) United States Patent
Qasba et al.

(10) Patent No.: US 7,153,500 B2
(45) Date of Patent: Dec. 26, 2006

(54) PRODUCTION OF MEGAKARYOCYTES BY THE USE OF HUMAN MESENCHYMAL STEM CELLS

(75) Inventors: Pankaj Qasba, Columbia, MD (US); Mark A. Thiede, Forest Hill, MD (US)

(73) Assignee: Osiris Therapeutics, Baltimore, MD (US)

( * ) Notice: Subject to any disclaimer, the term of this patent is extended or adjusted under 35 U.S.C. 154(b) by 253 days.

(21) Appl. No.: 09/780,653

(22) Filed: Feb. 9, 2001

(65) Prior Publication Data

US 2001/0005591 A1    Jun. 28, 2001

Related U.S. Application Data

(63) Continuation of application No. 09/316,797, filed on May 21, 1999, now Pat. No. 6,225,119.

(60) Provisional application No. 60/086,420, filed on May 22, 1998, provisional application No. 60/108,308, filed on Nov. 13, 1998.

(51) Int. Cl.
*A01N 63/00* (2006.01)
*A01N 65/00* (2006.01)
*C12N 5/00* (2006.01)

(52) U.S. Cl. .................. 424/93.21; 435/325; 424/93.1

(58) Field of Classification Search ................ 435/373, 435/372, 347, 325, 366, 320.1; 424/93.2, 424/93.7
See application file for complete search history.

(56) References Cited

U.S. PATENT DOCUMENTS 6,225,119 B1 *  5/2001   Qasba et al. ................ 435/373

OTHER PUBLICATIONS

Emerson Blood 87(8):3082-3088, 1996.*
Srour et al. Blood 82(11):3333-3342, 1993.*
Bertolini et al. Blood 89(8):2679-2688, 1997.*
Berenson et al. J. Clin. Invest. 81:951-955, 1988.*
Dexter et al. Ann. Rev. Cell Biol. 3:423-441, 1987.*
Cooper et al. Blood: in Principles and Practice of Hematology, pp. 1399-1401, J.B. Lippincott Company, Philadelphia, 1995.*
Hadin et al. Blood: in Principles and Practice of Hematology, pp. 172-176, J.B. Lippincott Company, Philadelphia, 1995.*
Stedman's Medical Dictionary, p. 1093, 26th Edition Williams & Wilkins, 1995.*
Ellis et al. Blood Reviews 9(1):1-6, 1995.*
Molineux et al. Blood 88(4):1509-1514, 1996.*
Developmental Biology, Fourth Edition, Chapter 9, pp. 354-359, Sinauer Associates, Inc. Publishers, Sunderland, MA.*
Lemoli et al. Acta Haematol 95:14-170, 1996.*
Villeval et al. Blood, 90(11):4369-4383, 1997.*
Molineux et al. Stem Cells 15:43-49, 1997.*

* cited by examiner

*Primary Examiner*—Joseph Woitach
(74) *Attorney, Agent, or Firm*—Elliot M. Olstein; Raymond J. Lillie

(57) ABSTRACT

The present invention is directed to hematopoietic progenitor cells isolated from a tissue specimen, such as marrow cells or peripheral blood, and to the method of co-culturing isolated hematopoietic progenitor cells with human mesenchymal stem cells to induce megakaryocyte differentiation and platelet production. In addition, hematopoietic stem cells can be genetically engineered to carry genes of interest particularly for the expression of physiologically active proteins. In the presence of mesenchymal stem cells, the transduced cells carry the new genetic material and express gene products that can be used to modulate blood disorders.

2 Claims, 6 Drawing Sheets

 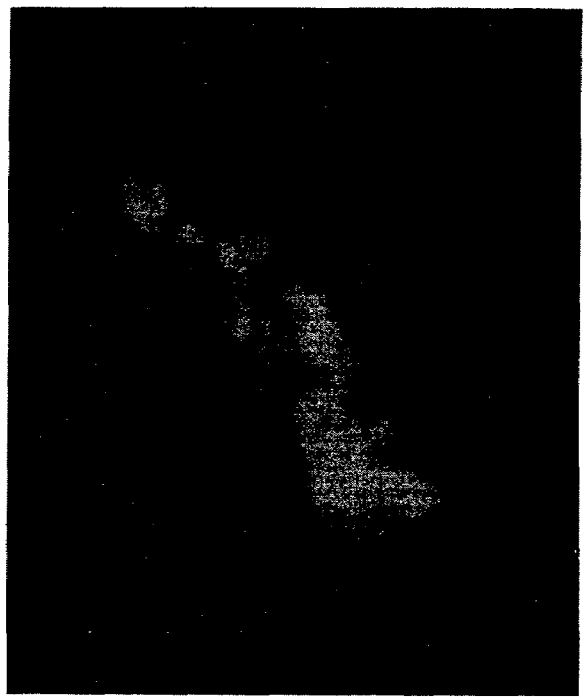
FIG.4A
FIG.4B

PRODUCTION OF MEGAKARYOCYTES BY THE USE OF HUMAN MESENCHYMAL STEM CELLS

This is a Continuation of application Ser. No. 09/316,797 filed May 21, 1999 now U.S. Pat. No. 6,225,119, which is based on U.S. Provisional Application No. 60/086,420, filed May 22, 1998 and U.S. Provisional Application No. 60/108,308, filed Nov. 13, 1998, upon which this application claims priority.

The present invention relates to the field of hematopoietic cell differentiation, and more particularly to the fields of megakaryocytopoiesis and thrombocytopoiesis. The present invention further relates to genetically modified hematopoietic stem cells in the presence of human mesenchymal stem cells, such that when the hematopoietic stem cells differentiate into megakaryocytes, the megakaryocytes are able to express the product of the transduced gene.

BACKGROUND OF THE INVENTION

The process of megakaryocytopoiesis is initiated with the terminal commitment of pluripotent hematopoietic stem cells (HSCs) into a differentiation pathway that results in the production of mature platelets into the circulation (Ellis, M. H. et al. *Blood*, 9:1–6 (1995). The events involve megakaryocyte proliferation followed by megakaryocyte maturation into platelets, and these processes are regulated by a number of cytokines with specific megakaryocytic maturational activity and a variety of cell adhesive interactions.

Factors known to support and regulate megakaryocyte growth and development include megakaryocyte growth and development factor and cytokines (Bertolini, F. et al. *Blood*, 89(8):2679–2688 (1997); Nagahisa, H. et al. *Blood*, 87(4):1309–1316 (1996)); and stromal cells (Guerriero, A. et al. *Blood*, 90(9):3444–3455 (1997)). A process which would facilitate the development and maturation of megakaryocytes into platelets which does not require the use of exogenous factors would be invaluable since the time to platelet recovery following bone marrow or peripheral blood progenitor transplantation can be very protracted.

SUMMARY OF THE INVENTION

The inventors have discovered that human mesenchymal stem cells (hMSCs) are capable of driving the process of megakaryocytopoiesis in vitro to produce megakaryocytes and platelets. Moreover, such a result can be achieved with or without the addition of exogenous cytokines or megakaryocyte maturation factors such as thrombopoietin (TPO). Human mesenchymal stem cells can support the maturation of co-cultured megakaryocytic precursor cells into platelets.

Accordingly, the present invention is directed to a method of co-culturing human mesenchymal stem cells in vitro with hematopoietic stem cells. The mesenchymal stem cells support the growth of the hematopoietic stem cells, their differentiation into megakaryocytes, and their maturation to platelets.

In another aspect, the present invention involves a method for treating a patient in need of megakaryocytes. In accordance with one aspect of the invention, human mesenchymal stem cells are administered in an amount effective to enhance the in vivo production of megakaryocytes from CD34+ cells. In accordance with another aspect of the invention, CD34+ megakaryocyte precursor cells are administered in the presence of mesenchymal stem cells to a subject in need thereof.

In another embodiment, the invention provides a method for treating a patient in need of platelets comprising infusing mesenchymal stem cells with or without hematopoietic stem cells, and thereafter administering TPO or other growth factors to induce or upregulate mesenchymal stem cells to signal hematopoietic stem cells to differentiate into megakaryocytes and further into platelets.

It has also been discovered that when hematopoietic stem cells, which have been modified to carry exogenous genetic material of interest, are co-cultured with mesenchymal stem cells, the transduced hematopoietic stem cells differentiate into megakaryocytes that also carry the new genetic material. These transduced megakaryocytes cells are able to express the exogenous gene product. Thus, transduced megakaryocyte progenitor cells, the megakaryocytes differentiated therefrom, and resultant platelets can be used for applications where treatment using such modified megakaryocytes is beneficial. For example, these modified cells can be used as a delivery system for therapeutic proteins encoded by the exogenous gene for treatment of inherited and/or acquired disorders of blood coagulation and wound healing, as well as pathogen defense.

Accordingly, the present invention provides a method of obtaining genetically modified megakaryocytes, comprising transducing hematopoietic progenitor cells with exogenous genetic material and placing the transduced hematopoietic cells under conditions suitable for differentiation of the hematopoietic stem cells into megakaryocytes which contain the exogenous genetic material.

In one embodiment, the method of producing megakaryocytes comprises co-culturing transduced hematopoietic stem cells with mesenchymal stem cells such that after differentiation of the hematopoietic stem cells into megakaryocytes, the megakaryocytes also contain the exogenous genetic material.

BRIEF DESCRIPTION OF THE DRAWINGS

FIG. 1A. The results of a 4 day culture of CD34$^+$ marrow cells

FIG. 1B. The results of a 4 day co-culture of MSCs and CD34$^+$ marrow cells.

FIG. 1C. Arrows point out dense cell clusters formed in the CD34$^+$ cell/MSC 4 day co-culture.

FIG. 1D. Proplatelets with extended cytoplasmic processes (arrow heads) are observed at high magnification in the CD34$^+$ cell/MSC 4 day co-culture.

FIG. 2A. A five day co-culture shows a single MSC associated with a CD34+ cell; double positive CD34+/41+ cells; and CD41$^+$ cells (two topmost arrowheads) are seen associated with MSCs.

FIG. 2B. Immunofluorescence analysis of a hMSC CD34$^+$ cell co-culture after 12 days. CD41$^+$ platelets are seen as small dots.

FIGS. 3A and B show the analysis of the CD34+ cell population at the start of the experiment.

FIGS. 3C and D show the analysis of a 5 day old culture of CD34+ cells alone.

FIGS. 3E and F show the analysis of a 5-day old culture of CD34+ with IL-3 (10 ng ml), IL-6 (10 ng/ml) and TPO (50 ng/ml).

FIGS. 3G and H show the analysis of cells recovered from MSC-CD34+ co-cultures.

FIG. 4. Photomicrographs of megakaryocytes and pro-platelets derived from co-culturing GFP-transduced CD34+ cells with MSCs.

FIG. 4A shows a phase contrast light microscope view of megakaryocytes with developed proplatelets.

FIG. 4B shows a fluorescence view of the same field. GFP expression in proplatelets is clearly visible.

DETAILED DESCRIPTION OF THE INVENTION

Figure 1:
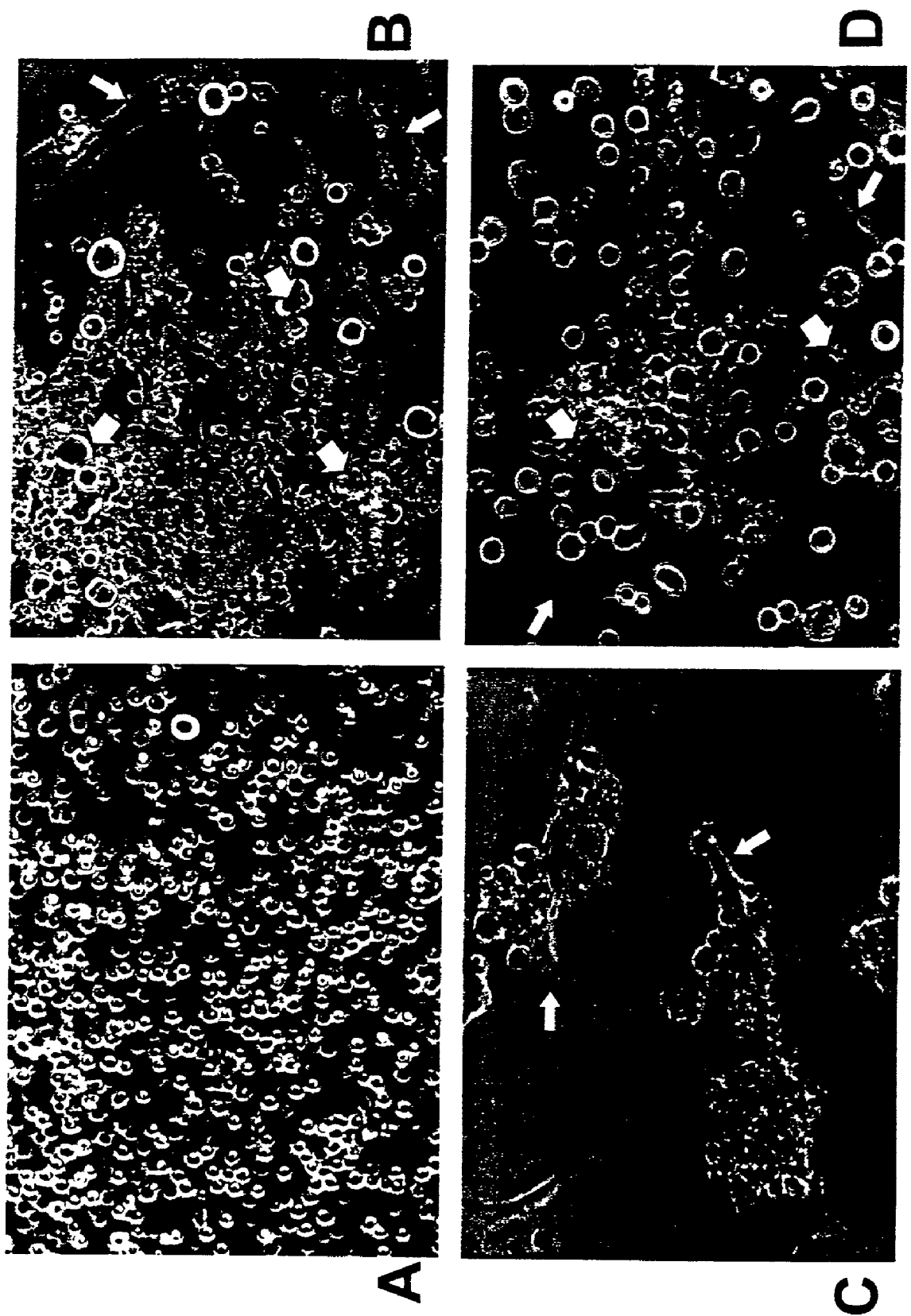
FIG. 1. Megakaryocytopoiesis and proplatelet formation in co-culture of hMSCs and CD34$^+$ cells.

The present invention relates generally to the use of human mesenchymal stem cells to cause human CD34+ cells to produce megakaryocytes preferentially and to compositions comprising human CD34+ and human mesenchymal stem cells.

More particularly, applicants have found that mesenchymal stem cells (MSCs) cultured in association with CD34+ cells drive the hematopoietic stem cells (HSCs) to differentiate selectively into megakaryocytes and ultimately to mature into platelets.

The inventors herein demonstrate successful hematopoietic cell differentiation and growth under suitable in vitro conditions in the presence of mesenchymal stem cells without adding exogenous cytokines or growth factors to the growth medium.

In order to obtain subject human mesenchymal stem cells for the methods described herein, mesenchymal stem cells can be recovered from other cells in the bone marrow or other mesenchymal stem cell source. Bone marrow cells may be obtained from iliac crest, femora, tibiae, spine, rib or other medullary spaces. Other sources of human mesenchymal stem cells include embryonic yolk sac, placenta, umbilical cord, fetal and adolescent skin, and blood. The presence of mesenchymal stem cells in the culture colonies may be verified by specific cell surface markers which are identified with unique monoclonal antibodies, see, e.g., U.S. Pat. No. 5,486,359. These isolated mesenchymal cell populations display epitopic characteristics associated only with mesenchymal stem cells, have the ability to regenerate in culture without differentiating, and have the ability to differentiate into specific mesenchymal lineages when either induced in vitro or in vivo at the site of damaged tissue.

The human mesenchymal stem cell populations can be allogeneic, or not donor matched to the hematopoietic stem cells, or the mesenchymal stem cells can be autologous to the hematopoietic stem cells.

Accordingly, any process that is useful to recover mesenchymal stem cells from human tissue may be utilized to result in a population of cells enriched for mesenchymal stem cells or comprising mostly mesenchymal stem cells. In one aspect, the method of isolating human mesenchymal stem cells comprises the steps of providing a tissue specimen containing mesenchymal stem cells, preferably bone marrow; isolating the mesenchymal stem cells from the specimen, for example by density gradient centrifugation; adding the isolated cells to a medium that stimulates mesenchymal stem cell growth without differentiation and allows, when cultured, for the selective adherence of the mesenchymal stem cells to a substrate surface; culturing the specimen-medium mixture; and removing the non-adherent matter from the substrate surface.

In a further aspect of the present invention, any process that is useful to recover, or alternatively co-recover hematopoietic progenitor cells and mesenchymal stem cells from human tissue may be utilized to result in a population of cells comprised mostly of hematopoietic cells. The human hematopoietic stem cells can be collected from bone marrow aspirates or peripheral blood and isolated using antibodies which may bind to hematopoietic stem cell surface antigens, e.g. CD34+, which are commercially available. For example, such antibodies may be conjugated to magnetic beads and immunogenic procedures utilized to recover the desired cell type. In this manner, hematopoietic stem or progenitor cells such as CD 34+ cells can be enriched by density gradient centrifugation and then detected and recovered by immunogenic procedures using an antibody specific for CD34+ cells.

According to the method of the present invention, the isolated mesenchymal stem cells and the isolated hematopoietic progenitor cells, preferably CD34+ cells, are each culture expanded in appropriate media, i.e. cultured by methods which favor cell growth of the enriched cell populations. In general, the cells are plated at a density of $0.1-2 \times 10^5$ cells/cm$^2$, preferably at a density of $1-2 \times 10^4$ cell/cm$^2$.

The cells may be characterized prior to co-culture to determine the composition of the cell population, for example by flow cytometric analysis (FACS). The human mesenchymal stem cells can be stained with human mesenchymal stem cell-specific monoclonal antibodies. The starting human mesenchymal stem cell population comprises about 70–80% human mesenchymal stem cells. In the case of hematopoietic stem cells, the cells are characterized by staining with the appropriate cell surface marker. The hematopoietic stem cell starting population should comprise approximately 50% or more of CD34+ hematopoietic stem/progenitor cells.

The human mesenchymal stem cells and the hematopoietic stem cells are then co-cultured under appropriate culture conditions, such that the mesenchymal stem cells adhere to a substrate surface and form a monolayer, and the CD34+ cells differentiate into megakaryocytes and further mature into platelets. The cells are grown in a ratio of human mesenchymal stem cells to hematopoietic stem cells of from about 10:1 to about 1:1. The MSCs may be cultured to confluency prior to addition of the CD34+ cells.

The culture conditions, such as temperature, pH, and the like, are those previously used with the cells utilized in this invention and will be apparent to one of skill in the art. Accordingly, the two cell populations are co-cultured in a medium that will support both cell populations and preferably not adversely affect either cell population.

In a particular embodiment, the cells are cultured in a medium that will not adversely affect the production of megakaryocytes. Suitable media include Iscove's minimum defined medium (IMDM) and supplements or Megacult (a serum free defined medium for human megakaryocytes and progenitors without cytokines). In a preferred embodiment, cells were cultured in BIT medium comprising Iscove's minimum defined medium supplemented with 10 mg/ml bovine serum albumin (BSA), 10 µg/ml human insulin, 200 µg/ml human transferrin, $10^{-4}$ 2-mercaptoethanol and 40 µg/ml low density lipoproteins.

In a most preferred embodiment, the culture medium preferably contains little or no serum. In the case where serum is present in the medium, in a preferred embodiment, the serum is present at a low concentration; generally the concentration of the serum being less than 7–8%, more preferably at no more than 4%, and most preferably at no more than 1%. In the most particularly preferred embodiment, the cell culture medium is essentially serum-free.

The megakaryocytes produced according to the methods described herein can be used for producing platelets and providing a reliable and constant source of platelet precursor cells for individuals in need thereof, e.g., those in need of transfusions of blood products or components, such as those individuals receiving chemotherapy, a bone marrow transplant or a peripheral blood stem cell transplant.

Another aspect of the present invention relates to the introduction of genes into the hematopoietic progenitor cells such that progeny of the cells, the megakaryocytes, carry the new genetic material.

In accordance with this aspect of the invention, the hematopoietic progenitor cells can be modified with genetic material of interest. The modified CD34+ cells can then be co-cultured in vitro with mesenchymal stem cells and induced to differentiate into megakaryocytes. The megakaryocytes are able to express the product of the gene expression or secrete the expression product. These modified cells can then be administered to a target, i.e., in need of platelets, where the expressed product will have a beneficial effect.

Genes can be introduced into cells which are then returned to the autologous donor or an allogeneic recipient where the expression of the gene will have a therapeutic effect. For example, megakaryocytes may be genetically engineered to express therapeutic proteins. Appropriate genes and their corresponding roles in treatment may include IL-2 for maintenance of T cell activation, treatment of cancer and HIV; EPO for erythropoeisis enhancement, dialysis support, post chemotherapy support; α-galactosidase A to provide metabolic enzyme for treating Fabry's disease, an inherited, lysosomal storage disorder; glucocerebrosidase, a metabolic enzyme to treat Gaucher Disease, an inherited disorder in which glucosylceramide accumulates; adenosine deaminase to prevent T cell death to treat ADA deficiency, an inherited immune disorder; and gp100, MART-1, tumor associated antigens, to treat forms of cancer.

The hematopoietic stem cells may be genetically modified (transduced or transformed or transfected) in the presence of the human mesenchymal stem cells, wherein the mesenchymal stem cells increase the efficiency of gene transduction of the hematopoietic stem cells. Alternatively, the hematopoietic stem cells may be transduced in the absence of the human mesenchymal stem cells.

Mesenchymal stem cells may be genetically modified to produce or upregulate factors that induce megakaryocytopoiesis. For example, the gene for TPO may be driven by a strong promoter such as the CMV promoter. This construct can be used to transduce the MSCs and so produce TPO constitutively at an increased level. Methods for transducing MSCs are described in U.S. Pat. No. 5,591,625.

The hematopoietic stem cells may be genetically modified by incorporation of genetic material into the cells, for example, using recombinant expression vectors. As used herein "recombinant expression vector" refers to a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in eukaryotic expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product.

The human hematopoietic progenitor cells and mesenchymal stem cells thus may have stably integrated a recombinant transcriptional unit into chromosomal DNA or carry the recombinant transcriptional unit as a component of a resident plasmid. Cells may be engineered with a polynucleotide (DNA or RNA) encoding a polypeptide ex vivo, for example. Cells may be engineered by procedures known in the art by use of a retroviral particle containing RNA encoding a polypeptide.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is MGIN, derived from murine embryonic stem cells. Generally regarding retroviral mediated gene transfer, see McLachlin et al. (1990).

The nucleic acid sequence encoding the polypeptide is under the control of a suitable promoter. Suitable promoters which may be employed include, but are not limited to, TRAP promoter, adenoviral promoters, such as the adenoviral major late promoter; the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; ITRs; the β-actin promoter; and human growth hormone promoters; the GPIIb promoter. The promoter also may be the native promoter that controls the gene encoding the polypeptide. These vectors also make it possible to regulate the production of the polypeptide by the engineered progenitor cells. The selection of a suitable promoter will be apparent to those skilled in the art.

It is also possible to use vehicles other than retroviruses to genetically engineer or modify the hematopoietic stem cells. Genetic information of interest can be introduced by means of any virus which can express the new genetic material in such cells. For example, SV40, herpes virus, adenovirus and human papillomavirus can be used for this purpose. Other methods can also be used for introducing cloned eukaryotic DNAs into cultured mammalian cells, for example, the genetic material to be transferred to stem cells may be in the form of viral nucleic acids.

In addition, the expression vectors may contain one or more selectable marker genes to provide a phenotypic trait for selection of transformed cells, such as dihydrofolate reductase, neomycin or green fluorescent protein (GFP).

The hematopoietic progenitor cells may be transfected through other means known in the art. Such means include, but are not limited to, transfection mediated by calcium phosphate or DEAE-dextran; transfection mediated by the polycation Polybrene (Kawai and Nishizawa 1984; Chaney et al. 1986); protoplast fusion (Robert de Saint Vincent et al. 1981; Schaffner 1980; Rassoulzadegan et al. 1982); electroporation (Neumann et al. 1982; Zimmermann 1982; Boggs et al. 1986); liposomes (see, e.g. Mannino and Gould-Fogerite (1988)), either through encapsulation of DNA or RNA within liposomes, followed by fusion of the liposomes with the cell membrane or, DNA coated with a synthetic cationic lipid can be introduced into cells by fusion (Feigner et al. (1987); Felgner and Holm 1989; Maurer 1989).

The present invention further makes it possible to genetically engineer human hematopoietic progenitor cells in such a manner that they produce, in vitro or in vivo, megakaryocytes that produce polypeptides, hormones and proteins not normally produced in human megakaryocytes, in biologically significant amounts, or polypeptides, hormones and proteins normally produced in small amounts in situations in which regulatory expression would lead to a therapeutic benefit. Alternatively, the cells could be modified such that a protein normally expressed will be expressed at much lower levels. These products are secreted into the surrounding media or purified from the cells. The human megakaryocytes produced in this way can serve as continuous short term or long term production systems of the expressed substance.

This technology may be used to produce additional copies of essential genes to allow augmented expression by the megakaryocytes of certain gene products in vivo. These genes can be, for example, hormones, matrix proteins, cell membrane proteins, cytokines, adhesion molecules, "rebuilding" proteins important in tissue repair. The expression of the exogenous genetic material in vivo, is often referred to as "gene therapy". Disease states and procedures for which such treatments have application include genetic disorders and diseases of blood and the immune system. Delivery of the transformed cells may be effected using various methods and includes intravenous or intraperitoneal infusion and direct depot injection into periosteal, bone marrow and subcutaneous sites.

In addition, as hereinabove described, the transduced cells may be used for in vitro production of desired protein(s).

After modification of the hematopoietic cells as described herein and induction of differentiation into megakaryocytes, the mixture of hematopoietic, megakaryocytes and mesenchymal stem cells may be separated to obtain a population of cells largely consisting of the transduced megakaryocytes. This may be accomplished by positive and/or negative selection of transduced hematopoietic cells using antibodies to identify hematopoietic cell surface markers.

The above description of the invention and the following examples are by way of illustration only. Other permutations and practices of the invention will be readily envisioned by one of ordinary skill in the art by view of the above in conjunction with the appended drawings. Therefore, such permutations and variations are within the scope of the present invention.

EXAMPLES

Human bone marrow aspirates routinely used for the isolation of the mesenchymal stem cells (MSCs) and CD34+ cells were purchased from Poietic Technologies, Gaithersburg, Md. Purified CD34+ cells approximately 96–98% pure, were also obtained from Poietic Technologies.

Example 1

Human MSCs were isolated and cultured according to known methods (e.g., Haynesworth et al. 1992). Briefly, 25–50 ml of heparinized bone marrow aspirate was mixed with an equal volume of phosphate buffered saline (PBS) and centrifuged at 900×g for 10 minutes at room temperature. Washed cells were resuspended in PBS to a final density of $2 \times 10^7$ cells/ml and a 10 ml aliquot was layered over a 1.073 g/ml solution of Percoll (Pharmacia, Piscataway, N.J.) and centrifuged at 900×g for 30 minutes at 25° C. Mononuclear cells collecting at the interface were recovered, washed once in PBS, resuspended in human MSC medium and expanded as described in, e.g. U.S. Pat. No. 5,197,985. The cells were plated at a density of $3 \times 10^7$ cells/185 $cm^2$ flasks.

CD34+ cells were isolated from bone marrow aspirates using the CD34 Progenitor Cell Selection System (DYNAL) according to the procedure recommended by the manufacturer. Briefly, the bone marrow samples were diluted 1:2 with Hank's buffered saline (HBS) (Life Technologies). Cells were recovered by centrifugation suspended at a density of $2 \times 10^7$ cells/ml, and 10 ml aliquots were layered over a 1.077 gm/ml Ficoll (Pharmacia, N.J.) solution. The mononuclear cells in the buffy coat were recovered from the interface and processed for CD34 cell selection using the DYNAL cell selection system.

To determine if the mesenchymal stem cells interact with the megakaryocytic progenitor CD34+ cells, and to determine if mesenchymal stem cells play a role in driving the CD34+ cells towards megakaryocytic maturation or megakaryocytopoiesis, cultures of CD34+ cells, with and without hMSCs were set up in duplicate for immuno-histochemistry experiments. The cells were seeded in four welled chamber slides with 1000, and 2000 CD34+ cells in each well. The number of hMSCs in each well was kept constant at 2000 cells. Samples were incubated in Iscove's medium supplemented with 10 mg/ml bovine serum albumin (BSA), 10 ug/ml human insulin, 200 ug/ml human transferrin, (BIT medium, Stem Cell Technologies, British Columbia, Canada), $10^{-4}$ M 2-mercaptoethanol (Sigma), plus 40 ug/ml low density lipoproteins (LDL) (Sigma). The suspension cultures were incubated unperturbed, for from 5–12 days at 37° C. At the end of days 5 and 11, all adherent cells in each chamber were fixed, and stained as described below.

FIG. 1 shows a 4 day culture of $CD34^+$ cells in culture alone (A) or in co-culture with MSCs. Cell clusters of $CD34^+$ cells and MSCs were observed in the co-culture.

Co-cultures were set up with matched or unmatched donors for the two cell types using similar culture conditions. Co-cultures for the megakaryocytopoiesis assays were set up with $1–2 \times 10^5$ cells of the purified CD34+ cells from donor #X and the same number of hMSCs from donors #X or #Y in Megacult medium with no cytokines or BIT medium (both supplied by Stem Cell Technology). The latter media was supplemented with 40 ug/ml LDL and $10^{-4}$ M 2-mercaptoethanol. The co-cultures were set up with about 5 ml media, in six well tissue culture plates and the cells were incubated at 37° C. for the length of the experiment (5–12 days) in an atmosphere of 5% $CO_2$ in air in a humidified incubator. Each time point and sample variation (allogeneic or autologous) was set up in duplicate. To characterize the phenotype of the cultured cells (day 5 and day 12), the non-adherent cells from each well were removed and pooled with the respective washes. The adherent hMSCs from each well were dislodged with 0.5 mM EDTA in PBS and the FACS analysis for each of these samples was done separately. The cells were resuspended and carefully washed in FACS buffer twice before staining with anti-CD34-APC, and anti-CD41/61 conjugated to PE, respectively. Cells were fixed with 2% paraformaldehyde in the FACS buffer, before the FACS analysis.

The cells in suspension from the co-cultures were removed along with the media and the adherent cell layer was washed twice with PBS. The washes were pooled with the cells in suspension and centrifuged at 500×g for 20 minutes. The adherent MSCs from the co-culture were trypsinized at room temperature and pelleted down at 900×g for 20 minutes. The cells were finally washed and collected in FACS buffer (PBS/2% bovine serum albumin/0.1% sodium azide) and incubated at RT for 20 minutes with 2 μg/ml of the primary antibodies, CD34-APC (Becton Dickinson, Mountain View, Calif.), CD41-PE and CD-61-FITC (PharMingen, San Diego). Cells were washed in the FACS buffer twice, and finally resuspended in 0.25 ml of the stop buffer. Cells were analyzed by collecting 10,000 events on a Becton Dickinson FACS instrument using Cell-Quant software.

Immunostaining was performed on the cells cultured in chamber slides. The cells were washed with PBS, taking care that the adherent cells/cell complexes were not dislodged. Cells were fixed in acetone on ice for 5 minutes, followed by two ten minute washes with PBS. Non specific sites were blocked with 5% normal goat serum, followed by the addition of appropriate antibody. The co-cultures were stained with three different antibodies. SH-3 antibody (conjugated to biotin) which recognizes a surface marker for hMSCs was used as the primary antibody followed by the addition of streptavidin conjugated to cascade blue as the secondary reagent. This was followed by two washes with PBS and addition of anti-CD41-PE and anti-CD34-FITC monoclonal antibodies. Staining of the hMSC/megakaryocyte cell-complexes was done with SH-3-FITC and anti-CD41-PE, as described above. All samples were incubated in the dark for 20 minutes at room temperature. The slides were washed in PBS for an additional 20 minutes before mounting in Aquamount and visualized under the microscope.

The results clearly demonstrated a strong physical association between the CD34+ cells and the MSCs. No appreciable difference was observed in the cell-cell binding of the allogeneic or autologous cultures. Both allogeneic and autologous cultures showed cell-complexes comprised of CD34+ cells associated with MSCs with equal frequency. After 48 hours in culture, the MSCs were found associated with small clusters of CD34+ and CD34/41+ cells, and within 5 days large lobulated cells were visible. Although the number of larger cells seen at day 5 did not dramatically change at day 12, dense clusters of CD41/61+ platelets that were released in the culture were observed at this time point. In contrast, the CD34+ cells alone under identical culture conditions did not show an appreciable increase in the cell size or number. However, the CD34+ bone marrow cells without MSCs appeared apoptotic.

Figure 2:
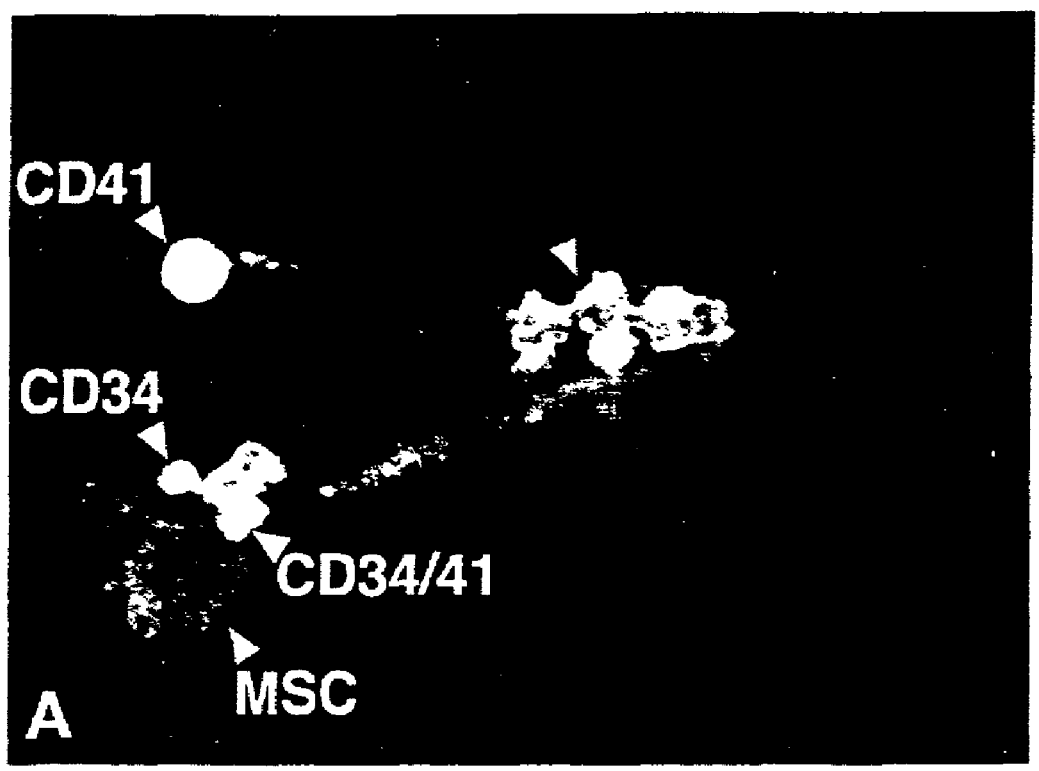
FIG. 2. Triple immuno-fluorescence analysis of MSC supported megakaryocytopoiesis. Five day co-cultures of MSCs and CD34$^+$ cells were incubated with biotinylated-monoclonal antibody SH-3, anti-CD41-PE and anti-CD34-FITC monoclonal antibodies that recognize MSCs, megakaryocytes, and CD34$^+$ cells, respectively. Streptavidin-conjugated to cascade blue was used as the fluorochrome for SH-3. Double positive CD34/41$^+$ cells are indicated.
Figure 2:
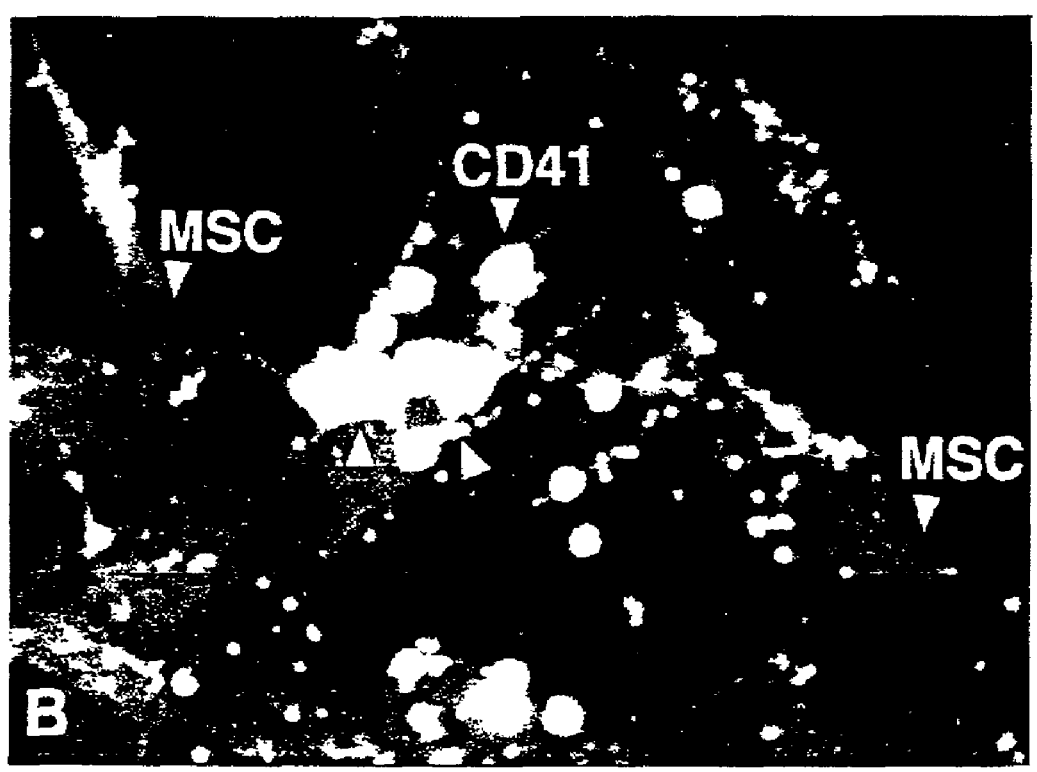

To address whether MSCs could support CD34+ and megakaryocytic differentiation in a defined media, the co-cultures were analyzed by immunostaining, i.e. triple immuno-fluorescence was performed. Staining on day 5 or day 12 with SH-3 cascade-blue, anti-CD41-PE and anti CD34-FITC monoclonal antibodies was performed on co-cultures to monitor MSC associated differentiation of the megakaryocytic precursor CD34+ cells. A distinct physical association between the MSCs and megakaryocytes was seen in addition to the FITC stained CD34+ cells that are also attached to the MSC. About 1% of the co-culture appeared to retain its CD34 positivity. See FIG. 2.

Immunostaining the cells in co-culture showed the expression of CD41 or CD61 surface markers in approximately 20% of the input CD34 cell population by day five. The number for differentiating cells (CD41+ or CD61+) did not substantially increase by day twelve, the duration of the co-cultures. Notably, most of the CD41 positive cells appeared to be closely associated with the MSCs in culture. The earliest production of platelets from the differentiated and maturing megakaryocytes was observed around day four, and the co-cultures showed a steady increase in platelet population up to day ten and eleven. Also, the starting cell population was virtually devoid of mature megakaryocytes. The frequency of double-labeled cells positive for both CD34+ markers and megakaryocytic markers was 3–5% seen by staining at day five and throughout the duration of the co-culture. However, only a small number (<1%) of the anchored hematopoietic stem cells to MSCs retained their CD34 marker.

The triple immune-fluorescence observations were further substantiated by FACS analysis that demonstrated that MSCs have a role in the regulation of megakaryocytic differentiation and platelet production.

Figure 3:
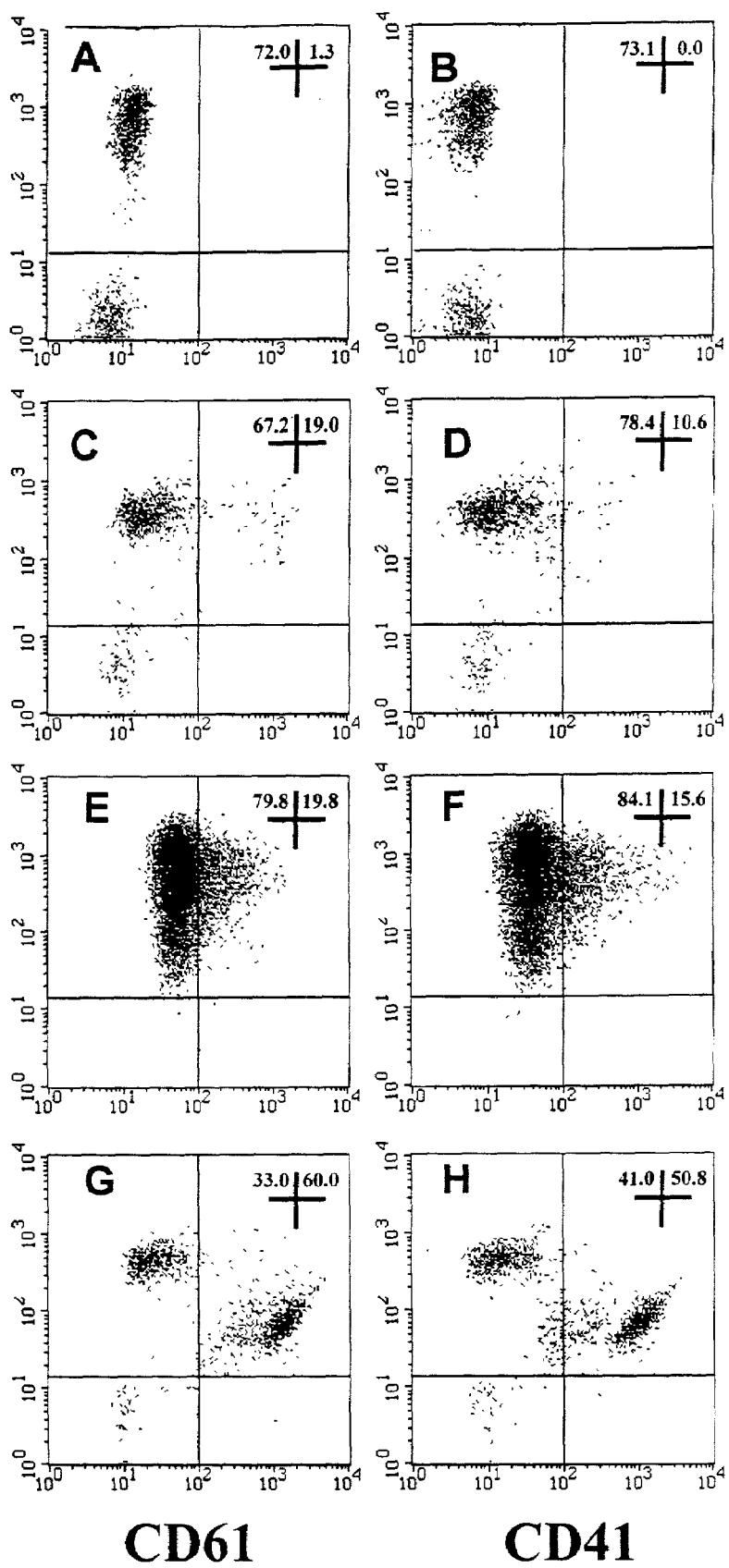
FIG. 3. Flow cytometric analysis of megakaryocyte differentiation from CD34+ cells co-cultured with or without hMSCs. Three color flow cytometry was performed on 5 day co-cultures using anti-CD34-APC (vertical axis), anti CD61-FITC and anti-CD41-PE (horizontal axis) antibodies. The numbers in the upper right hand corner of each dot plot indicate the percentage of the total CD34+ cells which are present in each quadrant.

The highly purified CD34+ cells (purity>96%) that were used for the co-culture experiments were analyzed for the presence of surface markers for megakaryocytic progenitors (CD34), megakaryocytic marker (CD41) and platelet markers (CD41/CD61). Both the size and positivity of the cells for the respective markers was analyzed. FACS analysis at days 0, 5 and 12 (FIG. 3) showed impressive progression of the cell phenotype from 2–6% CD41 + to more than 50% CD41+ on day 5–12. A more dramatic increase was seen with the number of platelets (CD41/CD61 double positive) within the co-cultures, present at days 5 and 12. Although a large number of cells still appeared to retain their CD34 phenotype, >10% were also CD41 or CD61 double positive.

FACS analysis of the co-cultures confirmed the appearance of platelets between days 5–12 by their dual reactivity to CD41 and CD61 markers. A majority of the platelets produced during the co-culture tended to adhere to the MSC cell layer. FACS data showed >50% of the CD41/CD61 signal was associated with the MSC stromal cell layer therefore making the quantitation of the platelet production difficult. Thus, both staining and FACS data confirmed the differentiated states of the starting CD34 cells towards the megakaryocytic lineage.

The method of Dolzhanskiya et al. *Blood*, 89:436–434 (1997) was slightly modified to evaluate ploidy. Briefly, non-adherent cells and the cells loosely attached to the hMSC monolayer were carefully dislodged from the co-cultures. The pooled cells were centrifuged for 20 minutes at 200× g and re-suspended in the FACS buffer. Cells were stained with anti CD41-FITC, permeablized and then fixed with 2% paraformaldehyde in PBS containing 160 ug/ml of isophosphatidylcholine (Lysolecithin, Sigma). Cells were incubated on ice for 5 minutes and washed with 5 volumes of Megacult medium. The cells were incubated overnight at 4° C. in the dark, with PBS containing 50 ug/ml of propidium iodide (PI) (Sigma). The cells were then incubated for 1 hour at room temperature in 100 ug/ml RNAse (GIBCO BRL), and the suspension was finally filtered through 100 μm nylon filter to remove aggregates. PI fluorescence data was compiled in logarithmic mode.

In the ploidy experiments, MSCs acted to increase the number of mitotic divisions for the differentiated megakaryocytes that took place before terminal differentiation and polyploidization. Control cultures with no MSCs and no exogenous cytokines showed an insignificant increase in ploidy.

Example 2

Figure 5:
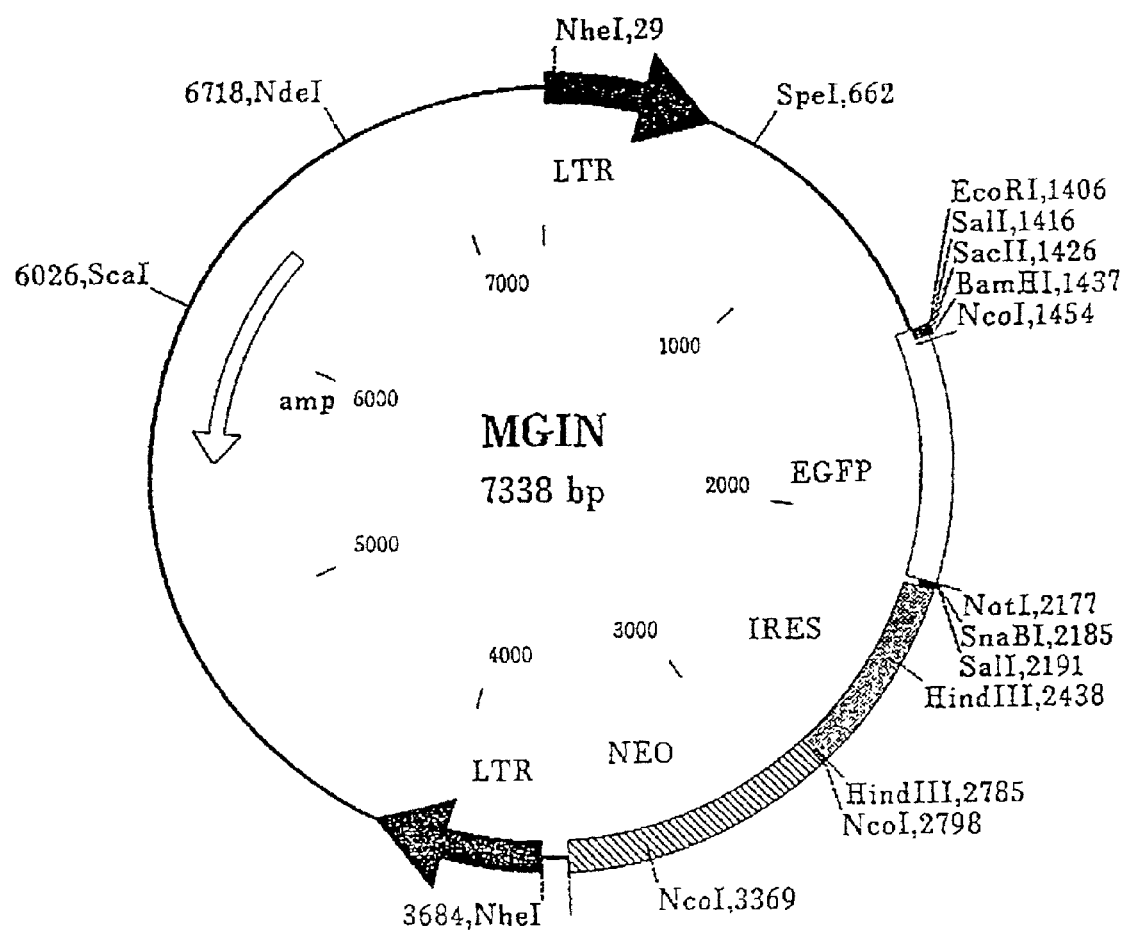
FIG. 5 shows a restriction map of the MGIN plasmid.

The following method was used to efficiently transduce purified human bone marrow CD34+ cells. Human CD34$^+$ cells were cultured in a serum-free medium and transduced with amphotropic retroviral supernates using a modification of the protocol described in *Gene Therapy*, 1997, 4:1013–1022. The retrovirus used was made with a murine stem cell virus (MSCV)-based vector containing the gene for enhanced green fluorescent protein (EGFP) (FIG. 5) and packaged in a 293 based human producer cell line.

CD34$^+$ cells isolated from human bone marrow were stimulated overnight in serum-free medium containing 1× BIT (Iscove's modified Dulbecco's medium with 1% bovine serum albumin, 10 μg/ml insulin and 200 μg/ml human transferrin, (Stem Cell Technologies Inc. Vancouver, B.C.), 0.01M β-Mercaptoethanol, 40 μg/ml low density lipoproteins (Sigma), and a combination of cytokines selected from the following: human IL-6, IL-3, G-CSF, stem cell factor (SCF), Flt3/flk2 ligand (FL) and thrombopoietin (TPO) (PeproTech Inc. Rocky Hill, N.J.). The cells were resuspended in tubes or tissue culture dishes in a 1:1 ratio of BIT-medium plus cytokines and the appropriate retroviral supernate. Polybrene was added at a final concentration of 8 μg/ml. Transduction was performed by centrifugation at 3000 rpm at 32°–38° C. for 2–4 h. The virus-containing medium was discarded and the cells were incubated in fresh medium overnight. Transduction was repeated with fresh retroviral supernate on the next day. The cells were then incubated in fresh medium with or without cytokines for the required time. In further experiments, CD34$^+$ cells were stimulated and transduced as a coculture on top of adherent hMSCs.

Transduction of CD34$^+$ cells with GFP

Human bone marrow derived CD34$^+$ cells (96–98% pure) were cultured and transduced in a serum-free medium containing a combination of SCF, FL, G-CSF, IL-3, IL-6, and TPO as described above. The pre-stimulated cells were inoculated on two consecutive days with amphotropic retroviral supernates. Control cells were treated similarly however in the absence of retrovirus. The cells were cultured for an additional two days after transduction. GFP and CD34 expression were analyzed by flow cytometry. The cells were stained with allophycocyanin (APC)-conjugated anti-CD34 antibody. The transduction efficiency varied in different experiments wherein 20 to 40% of the total cells expressed the transgene and 10 to 50% of the CD34+ cells expressed the transgene.

Transduced cells were also cultured on a monolayer of MSCs in serum free medium containing TPO. After two weeks of co-culture, the percentage of CD41+ cells increased to 43% of which 44% were also positive for GFP. GFP-labeled proplatelet structures were also observed.

Kinetics of CD34 and CD41 expression by CD34$^+$ cells cultured with cytokines.

CD34$^+$ cells (98% pure) were incubated in serum free BIT medium containing IL-3, IL-6, TPO, FL and SCF for 4 or 7 days. The total number of cells was counted at each time point. Expression of CD34 and CD41 was determined by flow cytometry using APC-conjugated anti-CD34 and PE-conjugated anti-CD41 antibodies. On day 4, 90% of the cells retained the CD34 marker while only 2% expressed both CD34 and CD41. No cells were positive for CD41 alone. By day 7, the percentage of cells expressing CD34 was reduced to 39%, and a negligible number of cells were CD41$^+$. These results show that a very small percentage of cells belonging to the megakaryocytic lineage were obtained by culturing CD34$^+$ cells in vitro with the combination of cytokines that were required for efficient transduction described above.

Effect of various cytokines on Transduction of hMSC-CD34$^+$ cell coculture.

Cocultures of hMSC-CD34$^+$ cells were prestimulated with various combinations of SCF, FL, IL-3, IL-6, G-CSF, and TPO and transduced in the presence of the same cytokines. On day 5, the cells were removed, counted and analyzed by flow cytometry for GFP and CD41 expression. Results showed that highest transduction levels and highest numbers of transgene expressing megakaryocytic cells were obtained with a combination of at least 5 cytokines, although TPO alone was sufficient for development of CD41$^+$ cells.

Expression of GFP-Transgene by proplatelets hMSCs (passage 1) were plated in 6 well dishes at 100,000/well. On the following day, purified CD34$^+$ cells from bone marrow (80,000 cells per 6 well dish) were added on top of the hMSCs. The coculture was pre-stimulated overnight with 2 ml of BIT serum free-medium containing IL-3 and IL-6 (10 ng/ml), SCF (50 ng/ml) and FL (20 ng/ml). Transduction with EGFP was performed as described above by replacing 1 ml of the medium with retroviral supernate. After transducing twice on consecutive days the CD34+ cells were removed and plated on fresh hMSCs (passage 2) and maintained in serum free medium +/−50 ng/ml TPO for an additional 11 days. Fresh BIT +/−TPO was added every 3–4 days. Several proplatelet like structures were seen in the cultures within 7 days. On day 11 the cultures were photographed for the presence of green fluorescent proplatelets. Some of the proplatelets expressed GFP as shown in FIG. 4, phase and fluorescent images of a proplatelet.

Time course of GFP-transgene expression in CD41$^+$ cells derived from transduced CD34$^+$ cells and cocultured with hMSCs.

Figure 6:
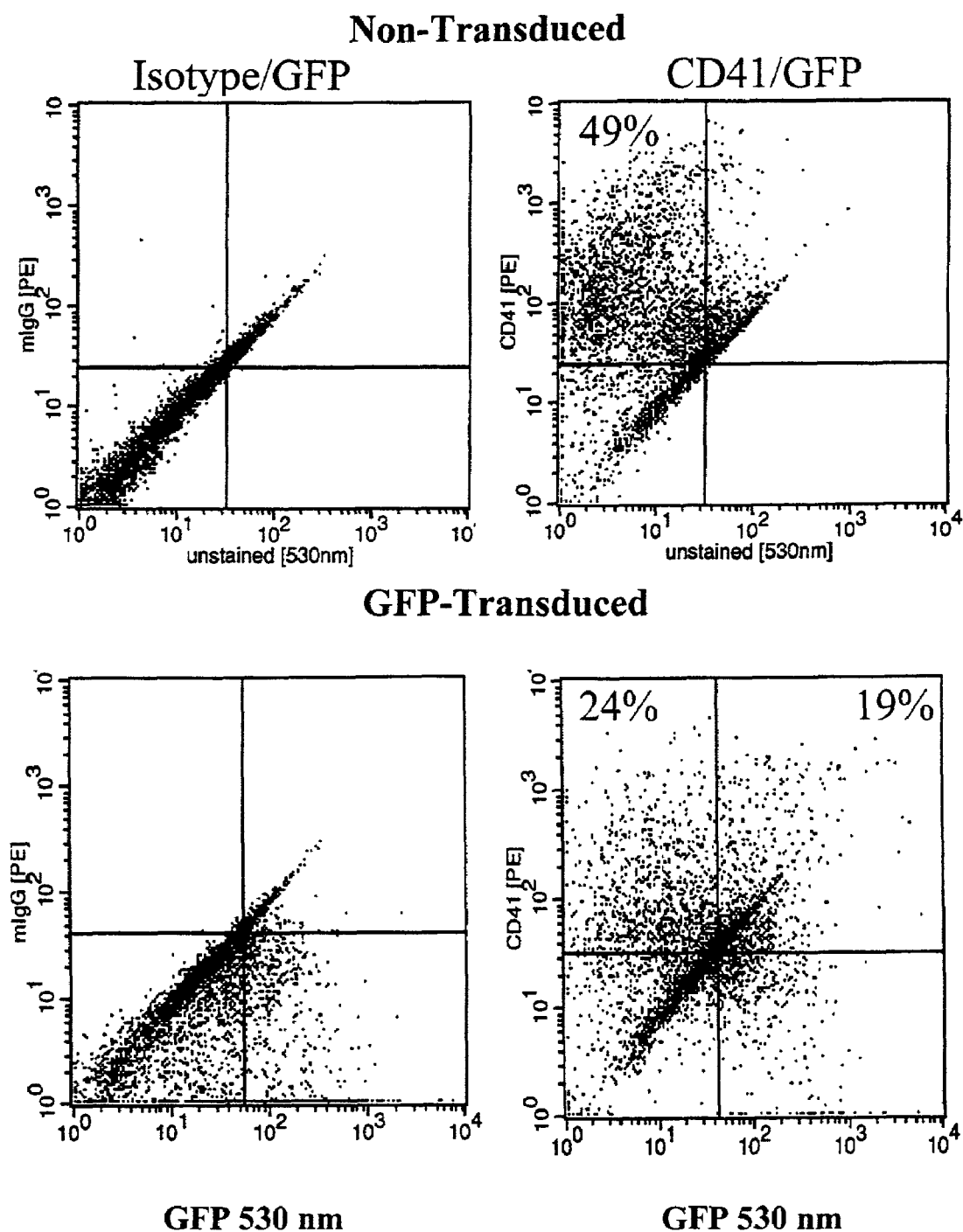
FIG. 6 shows the FACS analysis of transduced cells expressing CD41 and GFP compared to control cells.

CD34$^+$ cells were transduced in a hMSC/CD34$^+$ cell coculture in the presence of IL-3, IL-6, SCF, FL, G-CSF and TPO. The transduced CD34$^+$ cells were separated from hMSCs and added onto fresh hMSCs in the presence or absence of TPO. Microscopic observation showed the presence of several proplatelets, many of which expressed GFP. One week and two weeks later, the cells were analyzed for CD41 and GFP expression by flow cytometry. The results in Table 1 show a significant increase in CD41$^+$ cells with time and with addition of TPO (43% at 14 days). The percentage of CD41$^+$ cells expressing GFP was also significantly higher (19%) in the cocultures treated with TPO for 14 days. FIG. 6 shows the FACS profiles of transduced cells expressing CD41 and GFP, and non-transduced cells.

TABLE 1

Transgene Expression in CD41+ cells derived from Transduced CD34+ cells and Cocultured with hMSCs

|  | % GFP+ | | % CD41+ | | % GFP+CD41+ | |
|---|---|---|---|---|---|---|
|  | 7 days | 14 days | 7 days | 14 days | 7 days | 14 days |
| MSC + CD34 | 24 | 21 | 3.7 | 12 | 1.7 | 3 |
| MSC + CD34 + TPO | 26 | 15 | 14 | 43 | 6.1 | 19 |

GPIIb-promoter mediated expression of GFP-transgene in megakaryocytic cells.

The promoter region for the human GPIIb gene has been previously characterized (Uzan et al., 1991. J. Biol. Chem. 266:8932). Using genomic DNA as a template and appropriate primers, 624 bp of the proximal promoter and enhancer comprising −595 to +28 of GpIIb gene was amplified by PCR. The promoter was ligated into pCR2.1 and confirmed by sequencing. The promoter was cloned into pEGFP-1 (Clontech) to create a GPIIb-EGFP promoter-reporter cassette. SV40 polyadenylation sequence was added 3' of EGFP. This cassette was then cloned into a Moloney Leukemia virus retroviral vector (pN2*Neo), downstream of the Neomycin resistance gene in an antisense orientation to the 5' LTR, to produce pOT113. Retroviral supernates were produced in Retropack PT67 producer cell line (Clontech) by selection with G418.

In order to test GPIIb promoter-regulated expression of GFP specifically in GPIIb CD41-positive cells, two different hematopoietic cell lines were transduced. The HEL cell line is greater than 95% CD41+, whereas the Jurkat cell line is CD41-negative. Both cell lines were transduced with the GPIIb-EGFP retrovirus by centrifugation on two consecutive days as in the case of CD34+ cells. As a positive control the cells were transduced with a retrovirus expressing GFP constitutively from the 5' LTR. Two days after transduction the cells were stained with anti-CD41-PE and the expression of CD41 and GFP was determined. Results indicated that GPIIb-EGFP was expressed only in the CD41+ HEL cell line while the CD41-negative Jurkat cell line had no GFP expression off the GPIIb promoter. On the other hand, both the cell lines expressed GFP when transduced with the virus expressing GFP from the 5'LTR. Therefore, MK-specific gene expression was also obtained in CD41+ cells using GPIIb promoter driven GFP.

The above results demonstrate that the presence of the transgene product did not interfere with MK and platelet maturation and that a megakaryocyte-specific promoter may be used to drive cell or tissue specific exogenous gene expression.

The invention claimed is:

1. A method for treating a patient in need of megakaryocytes, comprising administering to the patient isolated and enriched human mesenchymal stem cells in an amount effective to produce megakaryocytes, wherein said mesenchymal stem cells are allogeneic or autologous to said patient.

2. A method for treating a patient in need of megakaryocytes comprising administering to the patient isolated and enriched human mesenchymal stem cells and CD34+ cells in an amount effective to produce megakaryocytes, wherein said mesenchymal stem cells are allogeneic or autologous to said patient.

* * * * *